(12) United States Patent
Wachtel et al.

(10) Patent No.: US 8,409,611 B2
(45) Date of Patent: Apr. 2, 2013

(54) PROCESS FOR CLEANING HARD GELATINE CAPSULES

(75) Inventors: Herbert Wachtel, Bingen (DE); Petra Schmidt-Joerg, Ingelhelm (DE); Volker Freudenberger, Schwabenheim (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 911 days.

(21) Appl. No.: 11/735,347

(22) Filed: Apr. 13, 2007

(65) Prior Publication Data

US 2007/0178157 A1 Aug. 2, 2007

Related U.S. Application Data

(63) Continuation of application No. 11/462,797, filed on Aug. 7, 2006, now abandoned, which is a continuation of application No. 10/162,977, filed on Jun. 6, 2002, now abandoned.

(60) Provisional application No. 60/303,473, filed on Jul. 6, 2001.

(51) Int. Cl.
*A61K 9/48* (2006.01)
*A61K 9/40* (2006.01)

(52) U.S. Cl. ........... 424/451; 424/452; 424/478; 604/58

(58) Field of Classification Search ........................ None
See application file for complete search history.

(56) References Cited

U.S. PATENT DOCUMENTS

| | | | | |
|---|---|---|---|---|
| 5,641,510 A | * | 6/1997 | Clark et al. | 424/451 |
| 6,537,524 B1 | * | 3/2003 | Hassan et al. | 424/45 |
| 6,585,959 B2 | * | 7/2003 | Walz et al. | 424/46 |

* cited by examiner

*Primary Examiner* — Lakshmi Channavajjala
(74) *Attorney, Agent, or Firm* — Michael P. Morris; Wendy A. Petka

(57) ABSTRACT

A process which can be used in the laboratory or on an industrial scale for cleaning the inner wall of hard gelatine capsules, in which the sealed capsules are cleaned with a powder formulation.

15 Claims, 1 Drawing Sheet

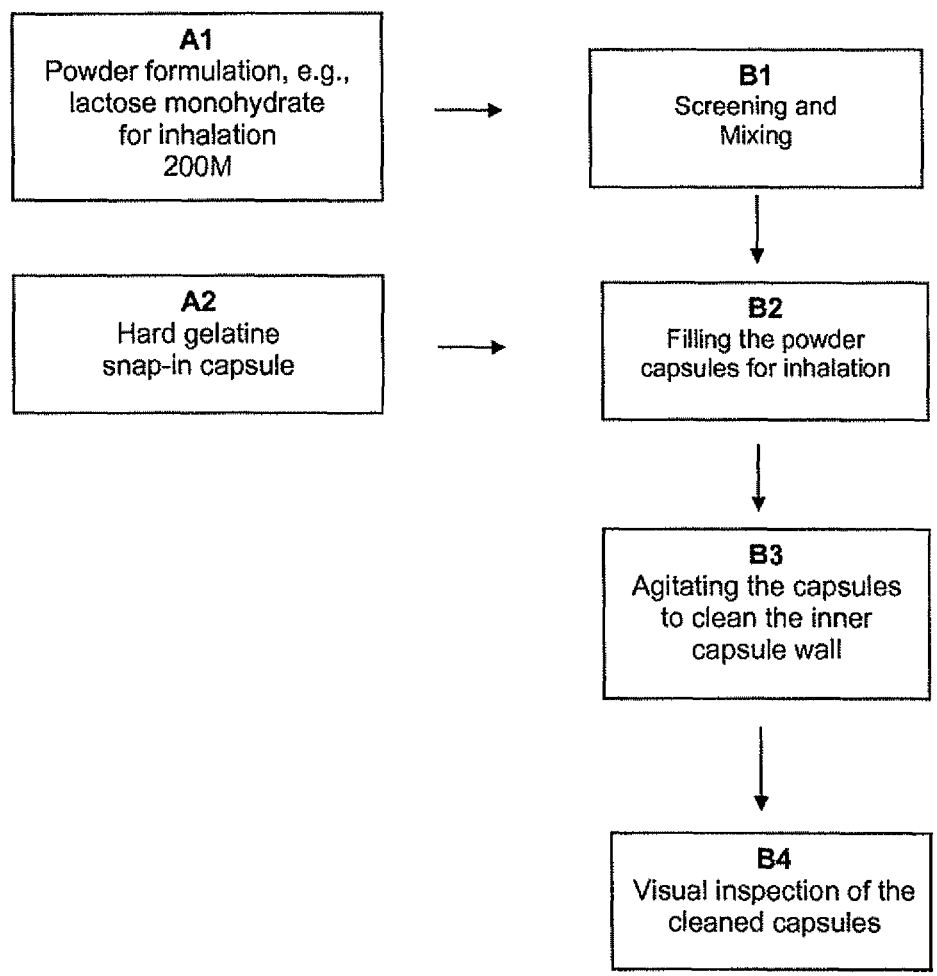

PROCESS FOR CLEANING HARD GELATINE CAPSULES

RELATED APPLICATIONS

This application is a continuation of U.S. application Ser. No. 11/462,797, filed Aug. 7, 2006, now abandoned, which is a continuation of U.S. application Ser. No. 10/162,977, filed Jun. 6, 2002, now abandoned. Benefit under 35 U.S.C. §119 (e) of prior provisional application Ser. No. 60/303,473, filed Jul. 6, 2001, is hereby claimed.

FIELD OF THE INVENTION

The invention relates to a process for cleaning the inner wall of hard gelatine capsules.

BACKGROUND OF THE INVENTION

As a result of the method of manufacturing hard gelatine capsules, the inner wall of these capsules is coated with lubricant and/or mould release agents. This leads to an increased adhesion of powder to the inner walls, which cannot be delivered to the patient in the case of capsules for inhalation. In addition, the parameters of "mass delivered" and "inhalable proportion" are subject to a wide range of fluctuations.

It is known from the prior art that special capsules, e.g., CONI-SNAP® two-piece gelatin capsules (Capsugel), which have a reduced coating of lubricant or mould release agent, can be used for inhalation purposes. This coating can be removed using solvents. However, cleaning with solvents is extremely expensive on an industrial scale and is therefore only suitable under certain conditions. In addition, the residual solvent content has to be checked thereafter.

The aim of the present invention is to provide a simple method of cleaning the inner wall of hard gelatine capsules for use in inhalation therapy.

BRIEF DESCRIPTION OF THE DRAWING

FIG. 1 is a flow chart illustrating a general process according to the invention.

DETAILED DESCRIPTION OF THE INVENTION

Surprisingly, it has now been found that the coating of lubricant or mould release agent can easily be removed from the inner walls of capsules by using suitable powders as cleaning agents without the addition of solvents.

The invention therefore relates to a process for cleaning the inner wall of hard gelatine capsules for use in inhalation therapy which can be carried out in the laboratory and also on an industrial scale, in which the capsules are cleaned with a powder formulation.

Capsules suitable for the process according to the invention are usually divisible hard gelatine capsules, consisting of an upper and lower part, in which the lower part is filled, then the top part is fitted on, and the capsule is sealed. Particularly suitable capsules are hard gelatine snap-in capsules with a closure, preferably polyethyleneglycol-free hard gelatine capsules, more preferably CONI-SNAP® two-piece gelatin capsules size 3 (made by Capsugel, division of Pfizer).

In a preferred process, the powder formulation is pharmaceutically acceptable. The powder formulation may contain one or more ingredients. Pharmaceutically acceptable ingredients include, for example, lactose, lactose monohydrate, glucose, sucrose, mannitol, and sorbitol.

Particularly preferred is a process wherein the powder formulation denotes an ingredient of the active substance formulation.

Ingredients of the active substance formulation which are suitable for the powder formulation include, for example, lactose, lactose monohydrate, glucose, sucrose, mannitol, and sorbitol, preferably lactose or lactose monohydrate, particularly lactose monohydrate.

Also preferred is a process wherein the powder formulation is the active substance formulation for inhalation.

Powders for inhalation may, for example, contain the active substances selected from among tiotropium, cromoglycic acid, reproterol, beclomethasone, terbutalin, salbutamol, salmeterol, ketotifen, orciprenaline, fluticasone, insulin, ipratropium, dexamethasone, bambuterol, budesonide, fenoterol, clenbuterol, prednisolone, prednisone, prednylidene, methylprednisolone, formoterol, and nedocromil, as well as one of the pharmaceutically acceptable salts or mixtures thereof and another cortisone preparation or atropine derivative suitable for inhalation purposes, preferably ipratropium bromide, tiotropium bromide, and tiotropium bromide monohydrate, particularly preferably tiotropium bromide monohydrate.

Typical ingredients of powders for inhalation, apart from the active substance, are lactose, lactose monohydrate, or glucose, inter alia.

Particularly preferred is a process wherein the cleaning takes place in sealed capsules.

Of particular importance is a process wherein the cleaning is carried out without the use of solvents.

Also of particular importance is a process wherein the cleaning is carried out in a gravity mixer or on a vibrating table. Gravity mixers which are suitable for the process according to the invention include, for example, ELTE 650 gyrowheel or SA 1200 gyrowheel (Messrs. Engelsmann AG, Frankenthaler Straße 137-141, D 6700 Ludwigshafen/Rh), Turbula T2 C (Messrs. Bachofen AG, Basle, Switzerland), or Turbula T 10 B (Messrs. Bachofen AG, Basle, Switzerland), while Turbula T2 C or Turbula T 10 B are particularly suitable.

Also of particular importance is a process wherein the cleaning is carried out at a temperature of 15° C. to 50° C., preferably 17° C. to 40° C., preferably 19° C. to 29° C., most preferably about 22° C.

Also preferred is a process wherein the mixing time is 20 minutes to 150 minutes, preferably 50 minutes to 100 minutes, preferably 60 minutes to 90 minutes, most preferably about 30 minutes to 75 minutes.

Also particularly preferred is a process wherein some or all of the grains of the powder formulation accumulate impurities.

Also preferred is a process wherein some or all of the grains of the powder formulation accumulate lubricants and mould release agents. Such lubricants and mould release agents may for example contain stearic acid, magnesium stearate, fats, waxes, oils, or emulsifiers such as soya lecithin.

Also particularly preferred is a process wherein the content of powder formulation is from 6% (v/v) to 50% (v/v), preferably 10% (v/v) to 30% (v/v), preferably 15% (v/v) to 25% (v/v), particularly preferably about 20% (v/v), of the maximum capacity of the capsule.

Also particularly preferred is a process wherein the powder formulation contains lactose and/or lactose monohydrate, preferably lactose monohydrate for inhalation purposes or preferably lactose monohydrate 200M for inhalation purposes. Lactose monohydrate may be obtained, for example, from Messrs. DMV International (Veghel/Netherlands).

According to the invention, a process is preferred wherein the powder formulation contains an excipient with particle sizes of 10 μm to 50 μm in aerodynamic diameter (measured with an API Aerosizer LD by a flying time method), for example, ground lactose monohydrate.

Particularly preferred according to the invention is a process which comprises the successive steps (a) to (e), wherein:
(a) a powder formulation is subjected to one or more screenings and mixings;
(b) the powder formulation is transferred into gelatine capsules for inhalation;
(c) the gelatine capsules are agitated in a mixing container;
(d) the end of the purification process is monitored visually, optionally by opening capsules; and
(e) the gelatine capsules are placed directly in the inhaler or optionally emptied and refilled.

The invention further relates to a gelatine capsule containing a tiotropium power formulation, obtainable by shaking the filled capsules in a gravity mixer or on a vibrating table.

The term tiotropium powder formulation refers to powder formulations of the tiotropium salts or the hydrates thereof, preferably the chloride, bromide, iodide, methanesulfonate, p-toluenesulfonate, or methylsulfate salt or the hydrates thereof preferably tiotropium bromide or tiotropium bromide monohydrate, most preferably tiotropium bromide monohydrate.

The invention further relates to the use of a capsule prepared by the process according to the invention in a powder inhaler, preferably in a Metered Dose Powder Inhaler (MDPI), particularly preferably in an MDPI as described in WO 94/28958.

The advantage of the process according to the invention is in the simple and economical cleaning of the inner wall of the capsule, which does not require any additional checking of the content of cleaning agent, e.g., solvent. In the case of pharmacologically acceptable contamination of the inner wall of the capsule, the cleaning may be done by the active substance formulation, so that the capsule does not have to be opened again after cleaning, emptied, and refilled with the active substance formulation. The cleaning process thus ensures, in this case too, a release of active substance which is not affected by the adhesion of the formulation to the inner wall of the capsules.

The process according to the invention can be carried out by the general procedure illustrated in the flow chart in FIG. 1 and according to the preferred embodiment described hereinafter. These are to be regarded as illustrating the invention without restricting it to their content.

For cleaning the gelatine capsules with a powder formulation using the process according to the invention, it is particularly suitable to use powder formulations which contain lactose monohydrate (A1) which has previously been mixed and screened.

For this, lactose monohydrate is screened through a suitable screen (B1), for example, a hand-held screen with a mesh size of 0.2 mm to 1 mm, preferably about 0.5 mm, or a suitable screening granulator with a mesh size of 0.2 mm to 1 mm, preferably about 0.5 mm to 0.6 mm, into a collecting container or mixing container. The screened material is homogeneously mixed in a suitable mixer, for example, in ELTE 650 gyrowheel or SA 1200 gyrowheel (Messrs. Engelsmann AG, Frankenthaler Straβe 137-141, D 6700 Ludwigshafen/Rh), Turbula T2 C (Messrs. Bachofen AG, Basle, Switzerland), or Turbula T 10 B (Messrs. Bachofen AG, Basle, Switzerland), over a period of 20 minutes to 150 minutes, preferably 50 minutes to 100 minutes, preferably 60 minutes to 90 minutes, particularly preferably about 30 minutes to 75 minutes, preferably at 5 revolutions per minute (rpm) to 35 rpm, preferably 10 rpm to 30 rpm, particularly preferably about 20 rpm. Suitable screening granulators which may be used include, for example, the QUADRO Comil, type: 197 S, 0.5 mm (Intertechnik Elze GmbH & Co KG, Lessingweg 1+2, D 31008 Elze) or Glatt Schnellsieb, type TR 80, 0.6 mm (Messrs. Glatt GmbH, D 7851 Binzen/Lörrach).

During the screening and mixing, the room should be maintained at a temperature of 19° C. to 28° C., preferably 22° C., and at a relative humidity of 35% r.h. to 65% r.h., preferably 50% r.h.

The screened lactose monohydrate is packed into snap-in gelatine capsules (A2), preferably polyethyleneglycol-free snap-in gelatine capsules, separately or as part of a powder formulation, using a suitable capsule filling and sealing machine (B2), for example, type MG2-G100 (Messrs. MG2, Bologna, Italy). The quantity of powder formulation packed in should be 6% (v/v) to 50% (v/v), preferably 10% (v/v) to 30% (v/v), preferably 15% (v/v) to 25% (v/v), particularly preferably about 20% (v/v), of the maximum capacity of the capsule. During filling, the climatic conditions in the room should be the same as for the screening and mixing process. The filled and sealed capsules are placed in a suitable mixing container under the climatic conditions described above. The fill level is 50% to 80%, preferably 60% to 70%, most preferably about 65%, of the height of the container.

The mixing container is then agitated in a suitable mixer (B3), preferably ELTE 650 gyrowheel or SA-1200 gyrowheel (Engelsmann AG, Frankenthaler Straβe 137-141, D 6700 Ludwigshafen/Rh), Turbula T2 C, or Turbula T 10 B (Messrs Bachofen AG (Switzerland) at 10 rpm to 30 rpm, preferably at about 20 rpm. The mixing time should be 20 minutes to 150 minutes, preferably 50 minutes to 100 minutes, preferably 60 minutes to 90 minutes, particularly preferably about 30 minutes to 75 minutes. The results of the mixing or cleaning process can be checked by visual inspection, optionally by opening capsules (B4). The cleaning process is complete as soon as no powder coating can be seen on the inner wall of the capsule. A very slight powder coating on the inner wall of the capsule is also sufficient for the cleaning process to be brought to an end.

The capsules may be emptied and then filled with an active substance formulation. If the active substance formulation itself is used as the powder formulation, there is no need to empty and refill the capsules. They may be used directly for inhalation.

The following Example serves to illustrate the process according to the invention. It is to be regarded as simply an example of procedure without restricting the invention to its content.

EXAMPLE

About 70 Grade A hard gelatine capsules (reduced content of lubricant and mould release agent), type CONI-SNAP® two-piece gelatin capsules size 3 (Capsugel) and about 70 Grade B (standard) hard gelatine capsules, type CONI-SNAP® two-piece gelatin capsules size 3 (Capsugel) were filled with a tiotropium-lactose mixture consisting of about 11 mg/capsule of lactose monohydrate (Pharmatose 200M made by Veghel/NL) and 36 μg/capsule of tiotropium bromide.

Half the capsules were shaken using with a Turbula Mixer type 2C (Messrs Bachofen AG, Basle, Switzerland) for about two hours at a temperature of 22° C. Then the parameter "dose delivered", i.e., the amount of active substance delivered in %, was determined in the shaken and unshaken capsules.

The results in Table I show a significant increase in the dose delivered (determined according to TEST Uniformity of Dose, a. Uniformity of Delivered Dose, European Pharmacopoeia, Third Edition (1997), page 1770, published by the Council of Europe, 67075 Strasbourg Cedex, ISBN: 92-871-2991-6), after the cleaning process by shaking the capsules.

TABLE 1

| Capsule | Dose delivered [%] |
| --- | --- |
| Grade A unshaken | 74 |
| Grade A shaken | 82 |
| Grade B unshaken | 79 |
| Grade B shaken | 83 |

We claim:

1. A process for cleaning the inner wall of a hard gelatine capsule for use in inhalation therapy to at least remove lubricant or mould release agent thereon, wherein the process comprises:
   (a) screening one or more ingredients in a powder formulation with a screen;
   (b) mixing the ingredient or ingredients from step (a) in a mixer;
   (c) transferring the powder formulation obtained from step (b) into a gelatine capsule, wherein the powder formulation content in the gelatine capsule is from 6% (v/v) to 50% (v/v) of maximum capacity of the gelatine capsule;
   (d) placing multiple capsules from step (c) into a mixing container, and agitating the mixing container for about 20 minutes to 150 minutes, resulting in cleaning of the capsule walls at least by removing lubricant or mould release agent thereon;
   (e) visually monitoring the cleaning to a selected endpoint comprises opening the capsule to determine the point at which powder no longer can be observed on the capsule inner wall;
   (f) emptying and refilling the gelatine capsule with an active substance formulation; and wherein steps (a) through (f) are performed at a temperature of between about 15° C. and 50° C. and a relative humidity of between about 35% and 65%, and the cleaning step (d) is carried out without the use of solvents.

2. The process according to claim 1, wherein the powder formulation is pharmaceutically acceptable.

3. The process according to claim 1, wherein the active substance formulation is for inhalation.

4. The process according to claim 1, wherein the active substance formulation contains a tiotropium powder.

5. The process according to claim 1, wherein the cleaning step (d) is carried out in a sealed capsule.

6. The process according to claim 1, wherein the cleaning step (d) is carried out in a gravity mixer or on a vibrating table.

7. The process according to claim 1, wherein some or all of the grains of the powder formulation accumulate impurities.

8. The process according to claim 1, wherein some or all of the grains of the powder formulation accumulate lubricants and/or mould release agents.

9. The process according to claim 1, wherein the powder formulation contains at least one excipient with particle sizes of 10 μm to 50 μm in aerodynamic diameter.

10. The process according to claim 1, wherein the powder formulation contains lactose and/or lactose monohydrate.

11. The process according to claim 1, wherein the screen in step (a) has a mesh size of about 0.2 mm to 1 mm.

12. The process according to claim 1, wherein the mixer in step (b) rotates between about 5 rpm and 35 rpm.

13. The process according to claim 1, wherein the ingredient or ingredients are mixed for about 20 minutes to 150 minutes.

14. The process according to claim 1, wherein in step (d), a fill level of capsules in the mixing container is between about 50% and 80% of a height of the mixing container.

15. The process according to claim 6, wherein the gravity mixer is used between about 10 rpm and 30 rpm.

* * * * *